United States Patent [19]

Kamiya et al.

[11] Patent Number: 5,155,258
[45] Date of Patent: Oct. 13, 1992

[54] SUBSTITUTED BENZOIC ACIDS

[75] Inventors: Yoshio Kamiya, Kawasaki; Shigeru Futamura, Chiba; Shinichiro Takigawa, Funabashi; Norio Tanaka, Funabashi; Shuzo Shinke, Funabashi, all of Japan

[73] Assignee: Nissan Chemical Industries, Ltd., Tokyo, Japan

[21] Appl. No.: 700,956

[22] Filed: May 14, 1991

Related U.S. Application Data

[63] Continuation of Ser. No. 408,214, Sep. 18, 1989, abandoned.

Foreign Application Priority Data

Sep. 18, 1988 [JP] Japan ................................ 63-234651
Dec. 6, 1988 [JP] Japan ................................ 63-308069

[51] Int. Cl.$^5$ .............................................. C07C 63/10
[52] U.S. Cl. .................................... 562/429; 562/432
[58] Field of Search ............................... 562/432, 429

[56] References Cited

U.S. PATENT DOCUMENTS

| | | | |
|---|---|---|---|
| 3,729,508 | 4/1973 | Ziegler et al. | 562/429 |
| 3,793,311 | 2/1974 | Feit et al. | 562/429 |
| 4,898,973 | 2/1990 | Lee | 562/429 |

OTHER PUBLICATIONS

E. I. Heiba et al., "Oxidation of Metal Salts V.[1] Cobaltic Acetate Oxidation of Alkylbenzenes", Journal of the American Chemical Society, 91:24, Nov. 19, 1969, pp. 6830–6837.

*Primary Examiner*—Marianne M. Cintins
*Assistant Examiner*—Margaret J. Argo
*Attorney, Agent, or Firm*—Oliff & Berridge

[57] ABSTRACT

A process for producing substituted benzoic acids represented by General Formula II:

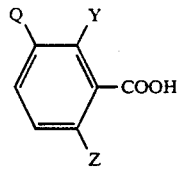

wherein Q represents a member selected from the group consisting of hydrogen, halogen atoms, —CN, —NO$_2$, —COOH, —COOR$_1$, —COR$_1$, —SR$_1$, —SO$_2$R$_1$ and —OR$_2$; and Y and Z each represents a member selected from the group consisting of halogen atoms, —CN, —NO$_2$, —COOH, —COOR$_1$, —COR$_1$, —SR$_1$, —SO$_2$R$_1$ and —OR$_2$ (in which R$_1$ represents an alkyl group containing 1 to 10 carbon atoms; and R$_2$ represents an alkyl group containing 1 to 10 carbon atoms or a phenyl group which may be substituted), which comprises oxidizing a substituted toluene represented by General Formula I:

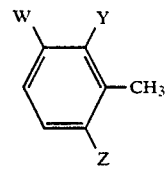

wherein W represents a member selected from the group consisting of hydrogen, halogen atoms, —CH$_3$, —CN, —NO$_2$, —COOH, —COOR$_1$, —COR$_1$, —SR$_1$, —SO$_2$R$_1$ and —OR$_2$; and Y and Z have the same meanings as defined above with an oxygen-containing gas in the presence of a metal compound catalyst.

1 Claim, No Drawings

SUBSTITUTED BENZOIC ACIDS

This is a continuation of application Ser. No. 07/408,214 filed Sep. 18, 1989, now abandoned.

BACKGROUND OF THE INVENTION

1. Field of the Invention

The present invention relates to a process for producing substituted benzoic acids useful as intermediates for medicaments or agricultural chemicals, e.g., herbicides.

2. Description of the Prior Art

It has been known that substituted benzoic acids can be produced by a process in which a substituted toluene is subjected to oxidation with an oxidizing agent, e.g., permanganates.

In the known process, however, oxidizing agents must be used in large excess, and the desired substituted benzoic acids can be produced at only a poor yield, e.g., as low as 40% or less. In addition, it is required to treat large quantities of waste water and manganese-containing wastes. Accordingly, the process is by no means suited for commercialscale production of substituted benzoic acids.

It has also been known that aromatic carboxylic acids can be produced from alkylbenzenes, such as toluene and xylene, by subjecting the latter to autoxidation with an oxygen-containing gas in the presence of a catalyst, such as cobalt acetate (see J. Am. Chem. Soc., 91, p. 6380 (1969).

However, it has not been known that toluenes having substituents at 2- and 6-positions thereof undergo autoxidation with an oxygen-containing gas. This may be attributable to the fact that it was generally presumed that autoxidation of 2,6-disubstituted toluene with an oxygen-containing gas would hardly proceed because of steric hindrance and electronic effects caused by the substitutional groups at the 2- and 6-positions thereof.

The present inventors have conducted intensive investigations on the autoxidation of substituted toluenes with an oxygen-containing gas and, as a result, have completed the present invention.

SUMMARY OF THE INVENTION

It is an object of the present invention to provide a process for producing 2,6-disubstituted benzoic acids through autoxidation of 2,6-disubstituted toluene with an oxygen-containing gas.

It is another object of the present invention to provide novel 2,6-disubstituted benzoic acids obtainable in accordance with the above process.

DETAILED DESCRIPTION OF THE INVENTION

Accordingly, there is provided by the present invention a process for producing substituted benzoic acids of Formula II,

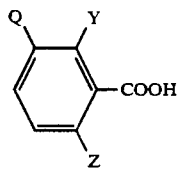

II wherein Q represents a member selected from the group consisting of hydrogen, halogen atoms, —CN, —NO$_2$, —COOH, —COOR$_1$, —COR$_1$, —SR$_1$, —SO$_2$R$_1$ and —OR$_2$; and Y and Z each represents a member selected from the group consisting of halogen atoms, —CN, —NO$_2$, —COOH, —COOR$_1$, —COR$_1$, —SR$_1$, —SO$_2$R$_1$ and —OR$_2$ (in which R$_1$ represents an alkyl group containing 1 to 10 carbon atoms; and R$_2$ represents an alkyl group containing 1 to 10 carbon atoms or a phenyl group which may be substituted), which comprises oxidizing a substituted toluene represented by General Formula I:

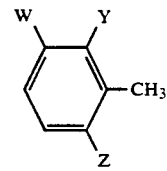

I (wherein W represents a member selected from the group consisting of hydrogen, halogen atoms, —CH , —CN, —NO$_2$, —COOH, —COOR$_1$, —COR$_1$, —SR , —SO$_2$R$_1$ and —OR$_2$; and R$_1$, R$_2$ and Z have the same meanings as defined above, with an oxygen-containing gas in the presence of a metal compound catalyst.

As examples of halogen atoms represented by Q, W, Y or Z in General Formulas I and II, mention may be made of fluorine, chlorine, bromine and iodine.

As examples of alkyl groups containing 1 to 10 carbon atoms represented by R$_1$ or R$_2$, mention may be made of methyl, ethyl, n-butyl, isopropyl, n-butyl, isobutyl, n-pentyl, isopentyl, n-hexyl, isohexyl, n-heptyl, isoheptyl, n-octyl, isooctyl, n-nonyl, isononyl, n-decyl and isodecyl groups.

As examples of substitutional groups which may be contained in the phenyl group represented by R$_2$ in the above General Formulae I and II, mention may be made of halogen atoms, —NO$_2$, —CN, —COOH, —COOR$_1$, —COR$_1$, —SR$_1$, —SO$_2$R$_1$, —OR$_2$, —NR$_1$R$_2$, —COR$_1$R$_2$, —CONR$_1$R$_2$, —SO$_2$NR$_1$R$_2$, —SO$_2$R$_1$, —CHX$_2$ and —CX$_3$ (in which R$_1$ and R$_2$ each represents an alkyl group of 1 to 10 carbon atoms, for exmple, methyl, ethyl, n-propyl, isopropyl, n-butyl, isobutyl, n-pentyl, isopentyl, n-hexyl, isohexyl, n-heptyl, isoheptyl, n-octyl, isooctyl, n-nonyl, isononyl, n-decyl, isodecyl or the like; and X represents a halogen atom, such as fluorine).

As preferable examples of compounds of the invention, mention may be made of those represented by General Formula I and having substitutional groups corresponding to one of the following combinations: W is hydrogen, halogen, —CH$_3$ or —COOH; Y is halogen; and Z is halogen or —SO$_2$CH$_3$.

More preferable examples of such compounds include those having substitutional groups corresponding to the following combinations: W is —CH$_3$ or —COOH; Y is halogen; and Z is —SO$_2$CH$_3$.

As examples of usable oxygen-containing gas, mention may be made of pure oxygen, air, and the like.

Partial pressure of oxygen in the oxygen-containing gas is usually from normal pressure to 80 kg/cm$^2$, preferably from normal pressure to 40 kg/cm$^2$.

As examples of metal compound catalysts usable in the above reaction, mention may be made of iron salts of aliphatic acids, such as iron formate, iron acetate, iron octylate, etc.; chelate compounds of iron, such as acetylacetonatoiron; inorganic iron salts, such as iron chloride, iron bromide, iron iodide, iron carbonate, etc.;

cobalt salts of aliphatic acids, such as cobalt formate, cobalt acetate, cobalt octylate, etc.; chelate compounds of cobalt, such as acetylacetonatocobalt, etc.; inorganic cobalt salts, such as cobalt chloride, cobalt bromide, cobalt iodide, cobalt carbonate, etc.; nickel salts of aliphatic acids, such as nickel formate, nickel acetate, nickel octylate, etc.; chelate compounds of nickels, such as acetylacetonatonickel; inorganic nickel salts, such as nickel chloride, nickel bromide, nickel iodide, nickel carbonate, etc.; manganese salts of aliphatic acids, such as, manganese formate, manganese acetate, manganese octylate; chelate compounds of manganese, such as acetylacetonatomanganese; inorganic manganese salts, such as manganese chloride, manganese bromide, manganese iodide, manganese carbonate, etc.; cerium salts of aliphatic acids, such as cerium formate, cerium acetate, cerium actylate, etc.; chelate compounds of cerium, such as acetylacetonatocerium; inorganic cerium salts, such as cerium chloride, cerium bromide, cerium iodide, cerium carbonate, etc.; zirconium salts of aliphatic acids, such as zirconium formate, zirconium acetate, zirconium actylate, etc.; chelate compounds of zirconium, such as acetylacetonatozirconium; and inorganic zirconium salts, such as zirconium chloride, zirconium bromide, zirconium iodide, zirconium carbonate, etc.

There is no particular restriction on the quantity of metal compound catalysts to be used. It can however be preferable to use a metal compound catalyst in an amount of from 1 to 20, more preferably from 2 to 10 gram-atoms, per 100 moles of compounds represented by General Formula I.

It is also possible to use a combination of the abovedescribed metal compound catalysts. For example, good results may be obtained by using a cobalt catalyst incorporated with from 1 to 1/20, preferably 1 to 1/10 gram-atoms of manganese.

It is also possible to additionally use a bromine compound and/or a carbonyl compound as a reaction accelerator.

As non-restrictive examples of usable bromine compounds, mention may be made of ammonium bromide, sodium bromide, potassium bromide, bromine and hydrogen bromide, as well as the above bromine compounds mentioned as examples of metal compound catalysts.

There is no particular restriction on the quantity of bromine compounds to be used. It can however be preferable to use from 1 to 20, more preferably from 1 to 10 moles of bromine compounds, per 100 moles of compounds represented by General Formula I.

As non-restrictive examples of usable carbonyl compounds, mention may be made of formaldehyde, acetaldehyde, methyl ethyl ketone, and the like.

There is no particular restriction on the quantity of carbonyl compounds to be used. It can however be preferable to use from 1 to 100, more preferably from 5 to 40 moles of carbonyl compounds, per 100 moles of compounds represented by General Formula I.

The reaction of the present invention is carried out preferably at a temperature of 20° to 200° C., more preferably 60° to 180° C.

The reaction of the present invention may be carried out either with or without solvents.

Operability and safety of the reaction may be improved by the use of a solvent.

Any stable solvent can be used for the reaction, including, e.g., lower aliphatic acids, such as acetic acid, propionic acid, butyric acid, etc.; and anhydrides of lower aliphatic acids, such as acetic anhydride, propionic anhydride, etc. Acetic acid can be particularly preferable.

In accordance with the process of the present invention, substituted benzoic acids represented by General Formula II can be readily obtained at a high yield from substituted toluenes represented by General Formula I.

The present invention can be particularly preferable in the cases where a compound in which Q is —COOH or bromine, Y is chlorine and Z is methanesulfonyl is obtained.

In these cases, there can be obtained 2-chloro-4-methanesulfonylisophthalic acid or 3-bromo-2-chloro-6-methanesulfonylbenzoic acid, which are novel and useful for producing herbicides (see Japanese Patent Application Nos. S62-61,349; S63-137,095; S63-148,921 and S63-195,676). Accordingly, the present invention also provides the two novel compounds.

Herbicides can be produced via the above compounds, in accordance with the following steps:

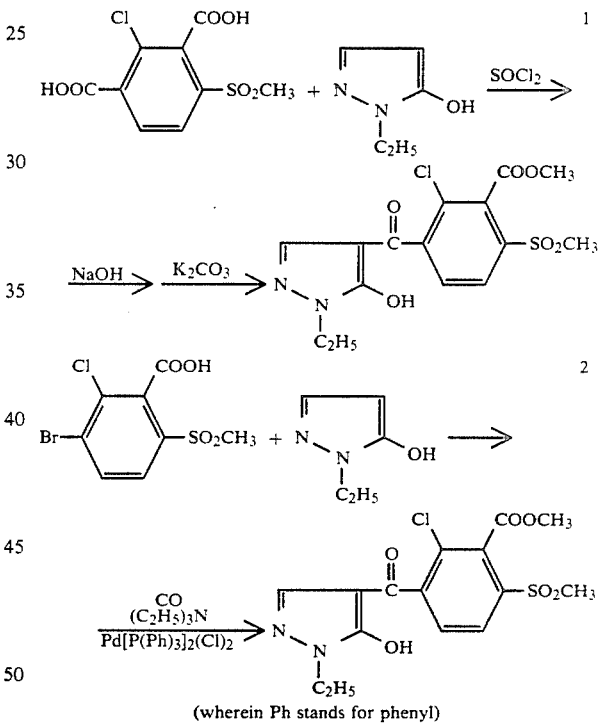

(wherein Ph stands for phenyl)

The compounds obtainable in accordance with the above reaction scheme possess excellent properties as herbicides.

The present invention will further be explained by way of examples. It should however be understood that the invention is by no means limited to these.

EXAMPLE 1

Into a 100 ml autoclave (made of Hastelloy C-76) were charged 11.95 g (50 mmol) of 3-bromo-2,6-dichlorotoluene, 0.498 g (2 mmol) of cobalt acetate, 0.123 g (1 mmol) of manganese acetate, 0.408 g (4 mmol) of sodium bromide and 50 ml of acetic acid.

Oxygen gas was supplied to the autoclave, and the contents of the autoclave were heated with stirring, allowing the reaction to proceed at 160° C. for 4 hours at a pressure of 40 kg/cm².

After the completion of the reaction, the reaction mixture was taken out and analyzed by gas chromatography. The conversion rate of 3-bromo-2,6-dichlorotoluene was 65%.

After the solvent in the reaction mixture had been removed off, part of the reaction product was esterified with diazomethane, and the product obtained was analyzed by means of GC-MASS. The analysis proved that the product formed was 3-bromo-2,6-dichlorobenzoic acid [M/e=284].

The yield of 3-bromo-2,6-dichlorobenzoic acid was 6.63 g (50%).

EXAMPLE 2

The procedure of Example 1 was repeated, except that 8.05 g (35.7 mmol) of 2,6-dichlorotoluene was used instead of 3-bromo-2,6-dichlorotoluene.

There were obtained a conversion rate of 2,6-dichlorotoluene of 95% and an yield of 2,6-dichlorobenzoic acid of 5.36 g (78.6%).

EXAMPLE 3

Into a 100 ml autoclave (made of Hastelloy C-276) were charged 14.13 g (50 mmol) of 3-bromo-2-chloro-6-methanesulfonyltoluene, 0.249 g (1 mmol) of cobalt acetate, 0.123 g (0.5 mmol) of manganese acetate, 0.204 g (2 mmol) of sodium bromide and 50 ml of acetic acid.

Oxygen gas was supplied to the autoclave, and the contents were heated with stirring, allowing the reaction to proceed at 150° C. for 4 hours at a pressure of 40 kg/cm².

After the completion of the reaction, the resulting reaction mixture was treated in the same manner as in Example 1.

The conversion rate of 3-bromo-2-chloro-6methanesulfonyltoluene was 87.0%, and the yield of 3-bromo-2-chloro-6-methanesulfonylbenzoic acid was 11.80 g (75.5%).

Analysis $^1$H-NMR (δ, ppm, CDCl$_3$-DMSO-d$_6$): 3.22 (3H, S), 7.9 (2H, A-Bq), 8.73 (1H, S)

EXAMPLE 4

Into a 100 ml autoclave (made of Hastelloy C-276) were charged 10.92 g (50 mmol) of 2-chloro-4-methanesulfonyl-m-xylene, 0.249 g (1 mmol) of cobalt acetate, 0.123 g (0.5 mmol) of manganese acetate, 0.204 g (2 mmol) of sodium bromide and 50 ml of acetic acid.

Oxygen gas was supplied to the autoclave, and the contents were heated with stirring, allowing the reaction to proceed at 160° C. for 4 hours at a pressure of 40 kg/cm².

After the completion of the reaction, the resulting reaction mixture was treated in the same manner as in Example 1.

The conversion rate of 2-chloro-4-methanesulfonyl-m-xylene was 92.0%, and the yield of 2-chloro-4methanesulfonylisophthalic acid was 9.12 g (65.5%).

Analysis $^1$H-NMR (δ, ppm, CDCl$_3$-DMSO-d$_6$): 3.20 (3H, S), 7.87 (2H, S), 9.26 (3H, brS)

Melting point: 200°-205° C.

EXAMPLE 5

Into a 100 ml autoclave ( made of Hastelloy C-276) were charged 12.43 g (50 mmol) of 2-chloro-3-methyl-4-methanesulfonylbenzoic acid, 0.24 g (1 mmol) of cobalt acetate, 0.123 g (0.5 mmol) of manganese acetate, 0.204 g (2 mmol) of sodium bromide and 50 ml of acetic acid.

Oxygen was supplied to the autoclave, and the contents of the autoclave were heated with stirring, allowing the reaction to proceed at 160° C. for 4 hours at an oxygen pressure of 40 kg/cm².

After the completion of the reaction, the resulting reaction mixture was treated in the same manner as in Example 1.

The conversion rate of 2chloro-3-methyl-4-methanesulfonylbenzoic acid was 90%, and the yield of 2-chloro-4-methanesulfonylisophtalic acid was 10.0 g (72.1%).

What is claimed is:

1. A compound represented by the following formula:

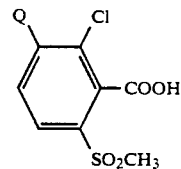

wherein Q represents a —COOH group.

* * * * *